United States Patent
Wolf et al.

(10) Patent No.: US 7,067,498 B2
(45) Date of Patent: Jun. 27, 2006

(54) POLYMER CONTROLLED INDUCED VISCOSITY FIBER SYSTEM AND USES THEREOF

(75) Inventors: Bryan W. Wolf, Johnstown, OH (US); Bruce B. Blidner, Westerville, OH (US); Keith A. Garleb, Pickerington, OH (US); Chron-Si Lai, Blacklick, OH (US); Timothy W. Schenz, Powell, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/157,297

(22) Filed: May 29, 2002

(65) Prior Publication Data

US 2003/0013679 A1    Jan. 16, 2003

Related U.S. Application Data

(63) Continuation-in-part of application No. 60/294,817, filed on May 31, 2001.

(51) Int. Cl.
*A61K 31/715* (2006.01)
*A61K 31/70* (2006.01)
*A61K 47/00* (2006.01)

(52) U.S. Cl. .............. 514/54; 514/2; 514/23; 514/57; 514/60; 514/775; 514/777; 514/778; 514/780; 514/781; 514/782; 514/866; 514/909; 536/2; 536/114

(58) Field of Classification Search ............. 514/54, 514/57, 60, 2, 23, 775, 777, 778, 780, 781, 514/782, 866, 909; 536/2, 114
See application file for complete search history.

(56) References Cited

U.S. PATENT DOCUMENTS

| | | | | |
|---|---|---|---|---|
| 4,556,578 A | * | 12/1985 | Meyer | ............ 426/649 |
| 4,766,207 A | * | 8/1988 | Deger et al. | ............ 536/18.6 |
| 4,921,877 A | | 5/1990 | Cashmere et al. | |
| 5,082,673 A | * | 1/1992 | Inglett | ............ 426/21 |
| 5,085,883 A | | 2/1992 | Garleb et al. | |
| 5,104,676 A | | 4/1992 | Mahmoud et al. | |
| 5,104,677 A | | 4/1992 | Behr et al. | |

(Continued)

FOREIGN PATENT DOCUMENTS

EP        0768043 A2    10/1996

(Continued)

OTHER PUBLICATIONS

Glytrol, 1995 Clintec Nutrition Company.

(Continued)

*Primary Examiner*—Shaojia A. Jiang
*Assistant Examiner*—Everett White
(74) *Attorney, Agent, or Firm*—William J. Winter; Thomas D. Brainard

(57) ABSTRACT

The present invention relates generally to a method of blunting the postprandial glycemic response in a human by feeding an induced viscosity fiber system. The invention also relates to an induced viscosity fiber system and the liquid products that incorporate the induced viscosity fiber system. Further, the invention relates to a method of incorporating soluble fiber into a liquid product without the typical negative organoleptic or physical stability issues. The invention also relates to a method of inducing the feeling of fullness and satiety by feeding the induced viscosity fiber system.

5 Claims, 6 Drawing Sheets

U.S. PATENT DOCUMENTS

| | | | |
|---|---|---|---|
| 5,204,135 A * | 4/1993 | Huang et al. ............... 426/589 |
| 5,292,723 A | 3/1994 | Audry et al. |
| 5,292,793 A | 3/1994 | Ramesh et al. |
| 5,389,391 A | 2/1995 | Monte |
| 5,470,839 A | 11/1995 | Laughlin et al. |
| 5,480,865 A * | 1/1996 | Kingham ....................... 514/2 |
| 5,776,887 A | 7/1998 | Wibert et al. |
| 6,020,017 A | 2/2000 | Mingione |
| 6,221,836 B1 | 4/2001 | Beale et al. |
| 6,248,375 B1 | 6/2001 | Giles et al. |
| 6,429,190 B1 * | 8/2002 | Portman ....................... 514/2 |
| 6,733,769 B1 | 5/2004 | Ryan et al. |

FOREIGN PATENT DOCUMENTS

| | | |
|---|---|---|
| JP | 03-290157 | 12/1991 |
| WO | WO 96/25054 | 8/1996 |

OTHER PUBLICATIONS

Compelling Comparisons Glucerna®, Mar. 1996, Ross Products Division, Abbott Laboratories.

PediaSure®, Mar. 2001, Pediatric Nutritionals Product Guide, Ross Products Division, Abbott Laboratories.

Choice*dm*™, 1997 Mead Johnson & Company.

Resource® Diabetic, 1995 Clinical Products Division, Sandoz Nutrition Corporation.

Compelling Comparisons Glucerna®, 1996 Ross Products Division, Abbott Laboratories.

Brutomesso, D,; Briani, G,; Bilardo, G,; Vitale, E,; Lavagnini, T,; Marescotti, C,; Duner, E,; Giorato, C,; Tiengo, A, The medium-term effect of natural or extractive dietary fibres on plasma amino acids and lipids in type I diabetics. *Diabetes Research and Clinical Practice*. 1989, 6, 149-155.

Krotkeiewski, M., Effect of Guar Gum on BodyWeight, Hunger Ratings and Metabolism in Obese Subjects. *Br. J. Nutr*, 1984, 52, 97-105.

"Fermentability of Various Fiber Sources by Human Fecal Bacteria In Vitro", American Journal Clinical Nutrition, 1991; 53: 14181424.

Ensure® Nutrition and Energy Bars, Dec. 2001, Ross Products Division, Abbott Laboratories.

U.S. Appl. No. 10/157,296, filed May 29, 2002.

U.S. Appl. No. 10/157,298, filed May 29, 2002.

The Alginate Reduce the Postprandial Glycaemic Response by Forming a Gel with Dietary Calcium in the Stomach of the Rat, *International Journal for Vitamin and Nutrition Research* (1997) 67 (1), 55-61.

JAPIO abstract AN 1991-290157 for JP 03-290157, Dec. 1991.

* cited by examiner

POLYMER CONTROLLED INDUCED VISCOSITY FIBER SYSTEM AND USES THEREOF

CROSS REFERENCE

This application is a continuation-in-part of U.S. patent application Ser. No. 60/294,817, which was filed on May 31, 2001. This application is related to the Acid Controlled Induced Viscosity Fiber System and Uses Thereof Ser. No. 10/157,296 and Dual Induced Viscosity Fiber System and Uses Thereof Ser. No. 10/157,298 continuation-in-part applications, filed concurrently herewith by Wolf et. al., the contents of which are herein incorporated by reference.

TECHNICAL FIELD

The present invention relates generally to a method of blunting the postprandial glycemic response to a meal. The invention also relates to an induced viscosity fiber system and the liquid products that incorporate the induced viscosity fiber system. Further, the invention relates to a method of incorporating soluble fiber into a liquid product without the typical negative organoleptic or physical stability issues. The invention also relates to a method of inducing the feeling of fullness and satiety by feeding the induced viscosity fiber system.

BACKGROUND OF THE INVENTION

Diabetes is the seventh leading cause of death in the United States and the sixth leading cause of death by disease among Americans. It is estimated that 15.7 million people, or 7.8% of the US population, suffer from diabetes. Consequently, the economic burden of diabetes is great, with an estimated total annual economic cost of $98 billion in 1997. This includes $44 billion for direct medical and treatment costs, and $54 billion for indirect costs due to disability and mortality.

The cause of diabetes is unknown, however, known risk factors for this disease are multi-factorial. Genetics and environmental factors such as obesity and sedentary lifestyle appear to contribute to diabetes incidence. Type 2 diabetes, a disorder resulting from the body's inability to make enough or properly use insulin, accounts for 90 to 95 percent of all diabetes. This type of diabetes is reaching epidemic proportions in America because of the increasing age of the population, in addition to a greater prevalence of obesity and sedentary lifestyles.

Standard treatment of diabetes involves maintenance of as near-normal blood glucose levels as possible by balancing food intake with insulin or oral glucose-lowering medications and physical activity levels. Low calorie diets and weight loss usually improve short-term glycemic levels and have the potential to improve long-term metabolic control. However, traditional dietary strategies, and even very-low-calorie diets, have usually not been effective in achieving long-term weight loss.

Obesity is associated with numerous chronic diseases, such as type 2 diabetes, heart disease, hypertension, stroke, dyslipidemia, osteoarthritis, sleep apnea, gallbladder disorders, respiratory problems, and malignancy. A loss of only 5% to 10% of baseline weight in an obese patient with type 2 diabetes, hypertension, or dyslipidemia can improve glycemic control, decrease blood pressure, and improve the lipid profile, respectively. Lifestyle modification by changes in diet or increase in exercise is usually the first step in treating overweight or obese persons. However, behavioral modification is often not very successful, and long-term maintenance of diet or exercise changes is attained by less than 15% of persons who initiate these changes. In addition, restricted calorie diets cannot be continued over a long period of time, and the majority of the weight lost on these diets is re-gained.

One approach to initiating and maintaining weight loss in overweight individuals is by inducing satiation (feeling of fullness during a meal) and satiety (feeling of fullness after a meal). Various gastrointestinal mechanisms trigger both the initiation and termination of eating in individual persons. Although gastric distention is a normal sign of "fullness" and plays a role in controlling food intake, its effects are temporary and distinct from feelings of satiety associated with a meal. Satiety is associated with postprandial sensations related to the activation of intestinal chemoreceptors, such as cholecystokinin, leptin, insulin, hypothalamic neuropeptide Y, and glucocorticoid hormones. These postprandial sensations, which are largely responsible for the phenomenon of satiation after a meal is consumed, have a longer-lasting effect on satiety or hunger than gastric distention.

The concept that dietary fiber may aid in the treatment of hyperglycemia has been suggested since the 1970's. Viscous soluble fiber (e.g., guar gum, psyllium, oat β-glucan) supplementation to test meals has been shown to effectively blunt postprandial glycemia. Despite the existence of some in vivo evidence; however, there is still considerable doubt about the efficacy of dietary fiber in the treatment of hyperglycemia. This doubt may exist because different types of dietary fibers have different physiological effects. As analytical methods for dietary fiber improve, so does our understanding of physiological fiber effects. For example, soluble viscous fibers generally have a greater effect on carbohydrate metabolism in the small intestine by slowing the rate of absorption, although delayed gastric emptying also may play a role. These phenomena should decrease the rate at which glucose enters the systemic circulation and delay the postprandial rise in blood glucose. While the applicability of this concept is evident, its clinical use is limited. Unfortunately, foodstuffs containing viscous fibers (e.g., guar gum) usually exhibit slimy mouth-feel, tooth packing, and poor palatability. The overall hedonic quality of guar-containing foods can be improved by reducing the average molecular weight (e.g., through chemical hydrolysis) of the galactomannan in guar gum; however, this results in a concurrent loss in clinical efficacy.

There are commercially available nutritional products that are designed to meet the nutritional needs of a diabetic while helping to maintain control of their blood glucose level. The commercial products are typically liquid and include higher amounts of fat. The higher fat is desired in a liquid nutritional as the fat slows down stomach emptying, thereby delaying the delivery of nutrients to the small intestine, which blunts the absorption curve of carbohydrates after a meal.

Glucerna® (Ross Products Division of Abbott Laboratories, Columbus Ohio) is a liquid nutritional with fiber for patients with abnormal glucose tolerance. Sodium and calcium caseinates make up 16.7% of total calories as protein; maltodextrin, soy polysaccharide and fructose make up 34.3% of total calories as carbohydrate; and high oleic safflower oil and canola oil make up 49% of total calories as fat. Soy polysaccharide contributes 14.1 g/1000 ml of total dietary fiber. The RDI for vitamins and minerals is delivered in 1422 kcals. The product also contains the ultra trace minerals selenium, chromium and molybdenum and the conditionally essential nutrients carnitine and taurine.

Choice dm® (Mead Johnson & Company, Evensville, Ind.) is a nutritionally complete beverage for persons with glucose intolerance. Milk protein concentrate makes up 17% of total calories as protein; maltodextrin and sucrose make up 40% of total calories as carbohydrate; and high oleic sunflower oil and canola oil make up 43% of total calories as fat. Microcrystalline cellulose, soy fiber and gum acacia contribute 14–4 g/1000 ml of total dietary fiber. The RDI for vitamins and minerals is delivered in 1060 kcals. The product also contains the ultra trace minerals selenium, chromium and molybdenum and the conditionally essential nutrients, carnitine and taurine.

Resource® Diabetic (Sandoz Nutrition Corporation, Berne, Switzerland) is a complete liquid formula with fiber specifically designed for persons with type 1 and type 2 diabetes and for persons with stress-induced hyperglycemia. Sodium and calcium caseinates, and soy protein isolate make up 24% of total calories as protein; hydrolyzed corn starch and fructose make up 36% of total calories as carbohydrate; and high oleic sunflower oil and soybean oil make up 40% of total calories as fat. Partially hydrolyzed guar gum contributes 3.0 g/8 fl. oz. of total dietary fiber. The RDI for vitamins and minerals is delivered in 2000 kcals. The product also contains the ultra trace minerals selenium, chromium and molybdenum and the conditionally essential nutrients carnitine and taurine.

Ensure® Glucerna® Shake (Ross Products Division of Abbott Laboratories, Columbus Ohio) is an oral supplement specifically designed for people with diabetes. Sodium and calcium caseinates and soy protein isolate make up 18% of total calories as protein; maltodextrin, fructose, maltitol, soy polysaccharide and FOS make up 47% of total calories as carbohydrate; and high oleic safflower oil and canola oil make up 35% of total calories as fat. Soy polysaccharide and fructooligosaccharides (FOS) contribute 3.0 g/8 fl. oz. of total dietary fiber. At least 25% of the DV for 24 key vitamins and minerals are delivered in 8 fl. oz. The product also contains the ultra trace minerals selenium, chromium and molybdenum.

U.S. Pat. No. 4,921,877 to Cashmere et al. describes a nutritionally complete liquid formula with 20 to 37% of total caloric value from a carbohydrate blend that consists of corn starch, fructose and soy polysaccharide; 40 to 60% of total caloric value from a fat blend with less than 10% of total calories derived from saturated fatty acids, up to 10% of total calories from polyunsaturated fatty acids and the balance of fat calories from monounsaturated fatty acids; 8 to 25% of total caloric value is protein; at least the minimum US RDA for vitamins and minerals; effective amounts of ultra trace minerals chromium, selenium and molybdenum; and effective amounts of carnitine, taurine and inositol for the dietary management of persons with glucose intolerance.

U.S. Pat. No. 5,776,887 to Wibert et al. describes a nutritional composition for the dietary management of diabetics containing a 1 to 50% total calories protein; 0 to 45% total calories fat, 5 to 90% total calories carbohydrate system and fiber. The carbohydrate system requires a rapidly absorbed fraction such as glucose or sucrose, a moderately absorbed fraction such as certain cooked starches or fructose and a slowly absorbed fraction such as raw cornstarch.

U.S. Pat. No. 5,292,723 to Audry et al. describes a liquid nutritional composition containing a lipid fraction, a protein fraction and a specific combination of glucides useful as dietetics. The glucide fraction consists of glucose polymers and slowly absorbed glucides.

U.S. Pat. No. 5,470,839 to Laughlin et al. describes a composition and method for providing nutrition to a diabetic patient. The low carbohydrate, high fat enteral composition contains a protein source, a carbohydrate source including a slowly digested high amylose starch and soluble dietary fiber and a fat source that includes a high percentage of monounsaturated fats.

U.S. Pat. No. 5,085,883 to Garleb et al. describes a blend of dietary fiber which includes by weight: 5% to 50% of a dietary fiber that is both soluble and fermentable; 5% to 20% of a dietary fiber that is both soluble and non-fermentable; and 45% to 80% of a dietary fiber that is both insoluble and non-fermentable. Preferably, the dietary fiber, which is both soluble and fermentable, is gum arabic; the dietary fiber, which is both soluble and non-fermentable, is sodium carboxymethylcellulose; and the dietary fiber, which is both insoluble and non-fermentable, is oat hull fiber.

U.S. Pat. No. 5,104,677 to Behr et al. describes a liquid nutritional product that contains a fat source and a dietary fiber system. The dietary fiber system as a whole includes by weight: (a) 5% to 50% dietary fiber which is both soluble and fermentable, 5% to 20% dietary fiber which is both soluble and non-fermentable, and 45% to 80% dietary fiber which is both insoluble and non-fermentable. Less than 10% of the total calories in the product comprise saturated fatty acids, no more than 10% of the total calories in the product is polyunsaturated fatty acids, and the ratio of the n-6 to n-3 fatty acids in the product being in the range of 2 to 10. Preferably the dietary fiber that is both soluble and fermentable, is gum arabic; the fiber that is both soluble and non-fermentable, is sodium carboxymethylcellulose, and the fiber that is both insoluble and non-fermentable, is oat hull fiber.

The prior art describes multi-component carbohydrate systems that blunt the glycemic response by requiring sources of carbohydrate that are absorbed at different rates. These multi-component carbohydrate systems possess physical characteristics that make incorporation of the carbohydrate systems into nutritional formulas difficult. Additionally, these multi-component carbohydrate systems are often found to possess unacceptable organoleptic characteristics. For example, guar gum functions to provide viscosity in the stomach, thereby slowing the release of nutrients to the small intestine. Unfortunately, foodstuffs containing guar gum typically exhibit slimy mouth-feel, tooth packing, and poor palatability. Additionally, effective amounts of guar gum increase the viscosity of liquid products such that the liquid product gels in the container. The overall hedonic quality of guar-containing foods can be improved by reducing the average molecular weight (i.e., through hydrolysis) of the galactomannan in guar gum; however, this results in a concurrent loss in clinical efficacy. In addition to the challenge of making a palatable product, dietary supplementation with effective levels of guar gum is also associated with gastrointestinal side effects (e.g., flatulence and diarrhea) from its colonic fermentation, because guar gum is a rapidly fermented carbohydrate.

Thus, a need has developed in the art for a fiber system which acts to blunt the absorption curve of carbohydrates after a meal, while being well tolerated, organoleptically acceptable and easily incorporated into nutritional matrixes. The formulation of these novel products that attenuate the postprandial glycemic excursion would enhance the use of nutrition as adjunctive therapy for people with diabetes mellitus.

The disease state of many diabetics is complicated by their overweight status. As described above, highly viscous digesta results in the slow release of nutrients to the small intestine. This slow release also induces the feeling of fullness and satiety. For example, 9 to 20 gm/day of supplemental guar gum for 4 to 8 weeks has been shown to significantly reduce body weight and sensations of hunger compared to control. (Bruttomesso, D.; Briani, G.; Bilardo, G.; Vitale, E.; Lavagnini, T.; Marescotti, C.; Duner, E.; Giorato, C.; Tiengo, A. The medium-term effect of natural or extractive dietary fibres on plasma amino acids and lipids in type 1 diabetics. *Diabetes Research and Clinical Practice.* 1989, 6, 149–155; Krotkiewski, M. Effect of guar gum on body-weight, hunger ratings and metabolism in obese subjects. *Br. J. Nutr.* 1984, 52, 97–105.) However, the same issues described above in tolerance and product development apply to the use of soluble fiber to induce the feeling of fullness and satiety. The commercial market responded to these organoleptic and product stability issues by manufacturing guar gum capsules. However, safety issues surfaced when the capsules were found to stick and swell in the throat upon swallowing. The increased incidence of choking resulted in the guar gum capsules being removed from the market.

Thus, a need has developed in the art for a fiber system that induces the feeling of fullness and satiety, while being well tolerated, organoleptically acceptable and easily incorporated into nutritional matrixes.

SUMMARY OF THE INVENTION

The inventors have discovered a novel fiber system that facilitates incorporation of soluble, viscous fibers into a liquid product. The novel fiber system is clinically effective in blunting the glycemic response to a meal while addressing the negative organoleptic, tolerance and physical stability issues typically associated with soluble viscous fibers. This novel system will be referred to as the induced viscosity fiber system. It is based upon building viscosity in vivo by the indirect action of α-amylase. The inventors discovered a system utilizing lightly hydrolyzed starch to prevent the dissolution of the soluble fiber. A low-viscosity shelf-stable, liquid product containing the induced viscosity fiber system of the instant invention was produced that became highly viscous when α-amylase was added to the product (i.e. an polymer controlled induced viscosity fiber system beverage). A product formulated with the induced viscosity fiber system of the invention has a low viscosity in the absence of α-amylase, be "drinkable", and become highly viscous following ingestion. It is upon ingestion that salivary a-amylase hydrolyzes the starch thereby enabling the fiber to solubilize and form a viscous digesta. Further, the induced viscosity fiber system requires less soluble fiber than the prior art to obtain the same clinical effect, thereby decreasing the tolerance and product development issues typically associated with soluble fiber. As discussed above, the induced fiber system of the instant invention would be applicable to people with diabetes and those needing to lose weight.

The first embodiment of the present invention refers to a polymer controlled induced viscosity fiber system. The first component of the induced viscosity fiber system of the instant invention is neutral soluble fiber. A second more soluble component is required for the polymer induced viscosity fiber system of the instant invention to function. Typically, the preferred more soluble component is lightly hydrolyzed starch. The concentration of the starch required to prevent the neutral soluble fiber from dissolving is inversely proportional to the molecular weight of the starch.

The present invention also refers to a method of delivering soluble fiber to diabetics and to persons needing to lose weight. The present invention also refers to a method of blunting the postprandial glycemic response by feeding induced viscosity fiber system. Additionally, the invention refers to a method of promoting the feeling of fullness by feeding the induced viscosity fiber system.

DETAILED DESCRIPTION OF THE INVENTION

Figure 1:
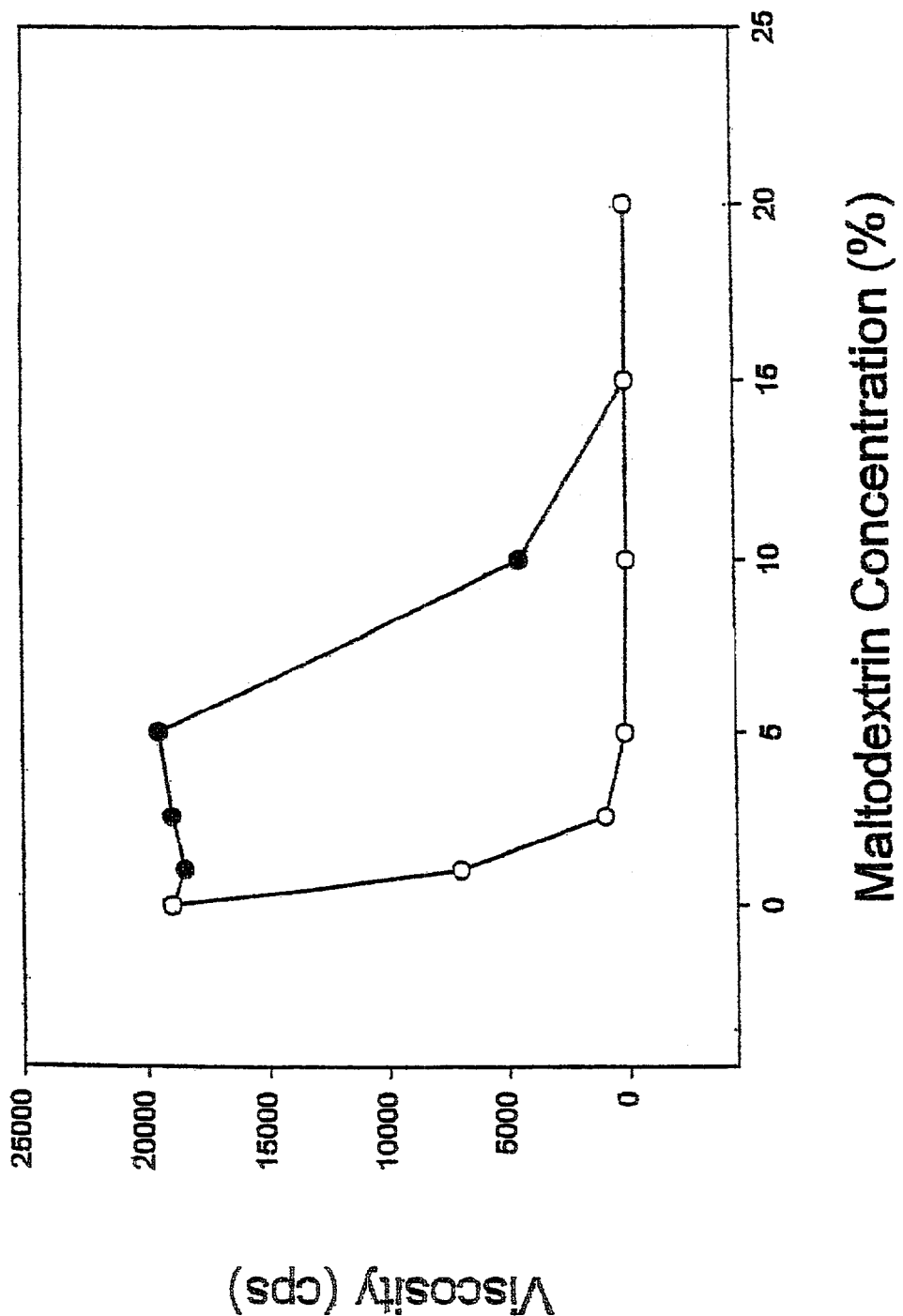
FIG. 1: Effect of carbohydrate molecular size and concentration on the viscosity of a guar gum solution. Maltodextrin with DP=25 (●) and maltodextrin with DP=100 ( ) added to a 2% guar gum solution.

As used in this application:
a. "glycemic index" (GI) is calculated by dividing the blood glucose incremental area under the curve (AUC) of the test food by the blood glucose AUC of the reference food and multiplying by 100, where the available carbohydrate content of test and reference foods are the same. The reference food is typically glucose or white bread, which has the standard GI of 100.
b. "neutral water soluble fiber" refers to fiber that can be dissolved in water and carries no charge at neutral pH.
c. "satiation" refers to the feeling of fullness during a meal. Various gastrointestinal mechanisms trigger the termination of eating in individuals. Although gastric distention is a normal sign of "fullness" and plays a role in controlling food intake, its effects are temporary and distinct from feelings of satiety associated with a meal.
d. "satiety" refers to the feeling of fullness after a meal. Satiety is associated with postprandial sensations related to the activation of intestinal chemoreceptors, such as cholecystokinin, leptin, insulin, hypothalamic neuropeptide Y, and glucocorticoid hormones. These postprandial sensations, which are largely responsible for the phenomenon of satiation after a meal is consumed, have a longer-lasting effect on satiety or hunger than gastric distention.
e. "soluble" and "insoluble" dietary fiber is determined using American Association of Cereal Chemists (AACC) Method 32-07. A "soluble" dietary fiber source refers to a fiber source in which at least 60% of the dietary fiber is soluble dietary fiber as determined by AACC Method 32-07, and an "insoluble" dietary fiber source refers to a fiber source in which at least 60% of the total dietary fiber is insoluble dietary fiber as determined by AACC Method 32-07.

f. "fermentable" and "non-fermentable" dietary fiber is determined by the procedure described in "Fermentability of Various Fiber Sources by Human Fecal Bacteria In Vitro", at AMERICAN JOURNAL CLINICAL NUTRITION, 1991; 53:1418–1424. This procedure is also described in U.S. Pat. No. 5,085,883 to Garleb et al. "Non-fermentable" dietary fiber refers to dietary fibers that have a relatively low fermentability of less than 40% by weight, preferably less than 30% by weight, and the term "fermentable" dietary fiber refers to dietary fibers which have a relatively high fermentability of greater than 60% by weight, preferably greater than 70% by weight.

g. the term "total calories" refers to the total caloric content of a definitive weight of the finished nutritional product.

h. the term "Reference Daily Intakes or RDI" refers to a set of dietary references based on the Recommended Dietary Allowances for essential vitamins and minerals. The Recommended Dietary Allowances are a set of estimated nutrient allowances established by the National Academy of Sciences, which are updated periodically to reflect current scientific knowledge.

i. the term "dextrose equivalence" (DE) refers to a quantitative measure of the degree of starch polymer hydrolysis. It is a measure of reducing power compared to a dextrose (glucose) standard of 100. The higher the DE, the greater the extent of starch hydrolysis. As the starch is further hydrolyzed (higher DE), the average molecular weight decreases and the carbohydrate profile changes accordingly. Maltodextrins have a DE less than 20. Corn syrup solids have a DE of 20 or higher and are more rapidly absorbed.

j. the term "degree of polymerization" (DP) refers to the number of glucose units joined in the molecule. The higher the DP average, the lesser the extent of starch hydrolysis. As the starch is further hydrolyzed, the average molecular weight decreases, the average DP decreases and the carbohydrate profile changes accordingly. Maltodextrins have a greater DP than corn syrup solids.

k. the term "starch" refers to the variety of cereal and root starches that contain a mixture of amylose and amylopectin starch molecules.

l. the term "lightly hydrolyzed starch" refers to a product obtained by acid, enzyme or combined hydrolysis of starch consisting of lower molecular weight polysaccharides, oligosaccharides and/or monosaccharides. Hydrolyzed starches typically include acid modified starches, acid thinned starches, thin boiling starches, dextrins and maltodextrins. The lightly hydrolyzed starches suitable for the instant invention typically have a DP of at least about 10.

m. the term "in vivo viscosity" refers to the viscosity measured by the addition of 20 μL of bacterial alpha-amylase (Sigma) to 250 gm of the polymer controlled induced viscosity fiber system followed by shearing using a Glass-Col mixer for 30 minutes. The viscosity following shearing is measured using a Brookfield Viscometer (Model DV-II+) with a 62 spindle at room temperature. The induced viscosity of nutritional products that contain the polymer controlled induced viscosity fiber system is measured by the addition of 20 μL of bacterial alpha-amylase (Sigma) to 250 gm of the nutritional product followed by shearing using a Glass-Col mixer for 30 minutes. The viscosity following shearing is measured using a Brookfield Viscometer (Model DV-II+) with a 62 spindle at room temperature.

n. the term viscosity is the ratio of shear stress to shear rate, expressed as dynes-second/$cm^2$, or poise. A centipoise (cps) is one hundredth of a poise. A poise is a unit of coefficient of viscosity, defined as the tangential force per unit area required to maintain one unit difference in velocity between two parallel planes separated by one centimeter of fluid. Any viscosity determination should be carried out using a Brookfield Viscometer (Model DV-II+) with a 62 spindle at room temperature. The viscosity is measured by operating the viscometer at a spindle speed that is the highest speed possible to obtain a reading that is on scale.

o. any reference to a numerical range in this application should be construed as an express disclosure of every number specifically contained within that range and of every subset of numbers contained within that range. Further, this range should be construed as providing support for a claim directed to any number, or subset of numbers in that range. For example, a disclosure of 1–10 should be construed as supporting a range of 2–8, 3–7, 5, 6, 1–9, 3.6–4.6, 3.5–9.9, 1.1–9.9, etc.

p. the terms "induced viscosity fiber system", "polymer controlled induced viscosity fiber system", "polymer induced viscosity fiber system" and "induced viscosity system" are used interchangeably and refer to the instant invention.

Hydrophilic polymers compete for water for solubilization. When two or more polymers are present in the same solution, the solubility of the less soluble polymer decreases as the concentration of the polymer with the higher solubility increases. When the concentration of the higher soluble polymer reaches a critical level, the less soluble polymer becomes insoluble. The advantage for a ready-to-feed (RTF) product is a high fiber content with a relatively low viscosity. The present invention relies on a "triggering" factor, that indirectly impacts the solubility of a soluble fiber to create induced viscosity in vivo.

The first component of the induced viscosity fiber system of the instant invention is neutral soluble fiber. Numerous types of dietary fibers are known and available to one practicing the art. Fibers differ significantly in their chemical composition and physical structure and therefore their physiological functions. The dietary fiber sources utilized in this invention can be characterized by the term solubility. Fiber can be divided into soluble and insoluble types and fiber sources differ in the amount of soluble and insoluble fiber they contain.

Representative of soluble dietary fiber sources are gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low and high methoxy pectin, β-glucans, carrageenan and psyllium. Numerous commercial sources of soluble dietary fibers are readily available and known to one practicing the art. For example, gum arabic, carboxymethylcellulose, guar gum, xanthan gum, alginates, pectin and the low and high methoxy pectins are available from TIC Gums, Inc. of Belcamp, Md. Oat and barley β-glucans are available from Mountain Lake Specialty Ingredients, Inc. of Omaha, Nebr. Psyllium is available from the Meer Corporation of North Bergen, N.J. while the carrageenan and konjac flour are available from FMC Corporation of Philadelphia, Pa.

Preferably, the soluble fibers of the instant invention are also neutral. Charged polymers are typically more soluble than neutral polymers, thus, neutral polymers are preferred for this application. Representative of neutral soluble dietary fiber sources are guar gum, pectin, locust bean gum, methylcellulose, β-glucans, glucomannan, and konjac flour.

All neutral water soluble fibers are suitable candidates for developing polymer controlled induced viscosity products. For example, as described in Experiment 3, the addition of maltodextrin drastically reduced the viscosities of locust bean gum, konjac flour, and methocel solutions.

The preferred neutral soluble fiber source is guar gum. Guar gum is a viscous, water-soluble dietary fiber composed of a β-1,4 mannose backbone with galactose side chains linked α-1,6. This galactomannan is obtained from the endosperm of the seeds of the leguminous vegetable, Indian cluster bean, *Cyamposis tetragonolobus*. It is widely used in the food industry as a stabilizer and as a thickening and film-forming agent.

A second more soluble component is required for the polymer induced viscosity fiber system of the instant invention to function. Typically, the preferred more soluble component is lightly hydrolyzed starch. The concentration of the starch required to prevent the neutral soluble fiber from dissolving is inversely proportional to the molecular weight of the starch. For example, as described in Experiment 1, 10% of the larger molecular weight, DP 100, maltodextrin was sufficient to render guar gum insoluble, while 15% of the smaller molecular weight, DP 25, maltodextrin was required to push the initially dissolved guar gum out of solution. Useful hydrolyzed starches of the instant invention typically comprise a DP of at least about 10, preferably of at least about 20, more preferably from about 40 to about 100.

Representative of suitable starch sources are cornstarch, potato starch, beet starch, rice starch, tapioca starch, and wheat starch and combinations thereof. Numerous commercial sources of starch and hydrolyzed starch are readily available and known to one practicing the art. For example, maltodextrin, glucose polymers, hydrolyzed cornstarch are available from Cerestar in Hammond, Ind. Wheat, rice and cornstarches are available from Weetabix Company in Clinton, Mass. Potato starch is available from Staley Mfg. Company in Decatur, Ill.

Alternatively, hydrolyzed starch may be obtained by acid, enzyme or combined hydrolysis of starch. One practicing the art would be aware of suitable hydrolysis methods. Typically, acid modified starches are made by mild acid hydrolysis of starch. For example, granular starch is suspended in very dilute acid and held at a temperature below its gelatinization temperature to yield an acid modified or thin boiling starch. Maltodextrins are typically prepared by partial hydrolysis of cornstarch with acids and enzymes. Dextrins are typically prepared by a process called pyrolysis, which involves a dry reaction with heat and acid.

Any single lightly hydrolyzed starch listed above, or any combination thereof may be utilized for developing induced viscosity fiber system of the instant invention. The ratio of neutral soluble fiber to lightly hydrolyzed starch is from about 0.35:5.0 to about 1:5.0, preferable from about 0.7:5.0 to about 1:5.0, more preferable about 1:5.0. Examples of suitable induced viscosity fiber systems include one part guar gum/five part DP100 maltodextrin; 0.35 part konjac flour/five part DP 100 maltodextrin; and 0.7 part guar gum/1.7 part DP100 maltodextrin/3.3 part DP25 maltodextrin.

Upon digestion, the induced viscosity fiber system is exposed to a-amylase, which begins to digest the lightly hydrolyzed starch, enabling the neutral soluble fiber to become solubilized. The induced viscosity fiber system of the instant invention generates a viscous digesta resulting in the slow release of nutrients into the small intestine. The slow release of nutrients into the small intestine results in prolonged absorption of nutrients, thereby blunting the glycemic response to the meal. The viscosity generated in vivo by the polymer controlled induced viscosity fiber system is at least about 300 cps, preferably at least about 1000 cps.

The induced viscosity fiber system has been designed to generate optimal viscosity in vivo while minimizing the ready-to-feed viscosity. As discussed previously, the more soluble lightly hydrolyzed starch forces the neutral soluble fiber out of solution, thereby producing an acceptable drinkable product. The ready-to-feed viscosity of the polymer controlled induced viscosity fiber system is less than about 300 cps, preferably less than about 200 cps, more preferably from about 50 cps to about 150 cps.

Typically the induced viscosity fiber system will be incorporated into food products and consumed by the diabetic during their meals or snack. If desired, the diabetic may simply modify the recipe of foods they normally consume. They may simply add the induced viscosity fiber system and thereby reduce the glycemic index of the food. A similar strategy may be utilized by individuals attempting to lose weight because the slow release of nutrients also induces the feeling of fullness and satiety.

Typically, the induced viscosity fiber system will be incorporated into meal replacement beverages such as Glucerna®, Ensure®, Choice DM®), Slim Fast®, Pediasure®, Glytrol®, Resource® Diabetic, etc. Methods for producing such food products are well known to those skilled in the art. The following discussion is intended to illustrate such diabetic and weight loss meal replacement products and their preparation.

The nutritional formulas of this invention are designed to be used as a meal replacement or as a supplement. Because the product can be used as a meal replacement it will contain a protein source, a lipid source, a carbohydrate source, and vitamins, and minerals. Such amounts are well known by those skilled in the art and can be readily calculated when preparing such products. While these meal replacement products may serve as the sole source of nutrition, they typically don't. Individuals consume these products to replace one or two meals a day, or to provide a healthy snack. The nutritional products of this invention should be construed to include any of these embodiments.

The amount of these nutritional ingredients can vary widely depending upon the targeted patient population (i.e. diabetics vs. non-diabetics, organoleptic considerations, cultural preferences, age group, use, etc.). Although not intended to limit the invention in any manner, but to merely serve as a general guideline, the nutritional formulas of this invention will typically provide the following caloric distribution. The protein system will typically provide from about 10% to about 35% of total calories, more preferably from about 15% to about 25% of total calories. The lipid system will provide less than about 37% of total calories, more preferably about 10% to about 30% of total calories. The carbohydrate system will typically provide from about 25% to about 75% of total calories, more preferably from about 35% to about 70% of total calories.

The novelty of these meal replacement products is the incorporation of the induced viscosity fiber system described above to generate a viscous digesta. As noted above, the carbohydrate will provide from about 25 to about 75% of total calories. Sufficient induced viscosity fiber system should be incorporated into the product so that the induced viscosity fiber system will comprise at least 10 w/w % of the carbohydrate system (when measured on a dry weight basis, i.e. not dissolved in a liquid). More typically, the induced viscosity fiber system will comprise from about 30 to about 60 w/w % of the carbohydrate system.

The remaining portion of the carbohydrate system may be provided by any carbohydrate system suitable for humans, taking into account any relevant dietary restrictions (i.e. if intended for a diabetic). Examples of suitable carbohydrates that may be utilized include glucose polymers, sucrose, maltitol, corn syrup solids, glucose, fructose, lactose, sugar alcohols, honey and high fructose corn syrup.

In addition to the carbohydrates described above, the nutritionals may also contain indigestible oligosaccharides such as fructooligosaccharides (FOS). Indigestible oligosaccharides are rapidly and extensively fermented to short chain fatty acids by anaerobic microorganisms that inhabit the large bowel. These oligosaccharides are preferential energy sources for most Bifidobacterium species, but are not utilized by potentially pathogenic organisms such as *Clostridium perfingens, C. difficile,* or *E. coli*. The term "indigestible oligosaccharide" refers to a small carbohydrate moiety with a degree of polymerization less than or equal to about 20 and/or a molecular weight less than or equal to about 3,600, that is resistant to endogenous digestion in the human upper digestive tract.

The meal replacement products also typically contain a protein source. The proteins that may be utilized in the nutritional products of the invention include any proteins suitable for human consumption. Such proteins are well known by those skilled in the art and can be readily selected when preparing such products. Examples of suitable proteins that may be utilized typically include casein, whey, milk protein, soy, pea, rice, corn, hydrolyzed protein and mixtures thereof. Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa.

One skilled in the art must consider the solubility of the protein source when selecting an appropriate protein source. For example, as described in Experiment 4, soluble proteins such as sodium caseinate can negatively impact the in vivo induced viscosity and insoluble proteins such as milk protein isolate can increase the induced viscosity.

The third component of the nutritional products of this invention is the fat. The fat source for the present invention may be any fat source or blend of fat sources suitable for human consumption. As noted above, the fat source of this invention will typically provide less than or equal to 37% of the total calories. The fat source for the present invention may be any fat source or blend of fat sources that provides the desired levels of saturated (less than 10% kcal), polyunsaturated (up to 10% kcal) and monounsaturated fatty acids (10% to 37% kcal). One skilled in the art can readily calculate how much of a fat source should be added to the nutritional product in order to deliver the desired levels of saturated, polyunsaturated and monounsaturated fatty acids. Examples of food grade fats are well known in the art and typically include soy oil, olive oil, marine oil, sunflower oil, high oleic sunflower oil, safflower oil, high oleic safflower oil, flaxseed oil, fractionated coconut oil, cottonseed oil, corn oil, canola oil, palm oil, palm kernel oil and mixtures thereof.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Organ. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Olive oil is available from Anglia Oils of North Humberside, United Kingdom. Sunflower and cottonseed oils are available from Cargil of Minneapolis, Minn. Safflower oil is available from California Oils Corporation of Richmond, Calif.

The nutritional compositions of the invention desirably contain vitamins and minerals. Vitamins and minerals are understood to be essential in the daily diet. Those skilled in the art appreciate that minimum requirements have been established for certain vitamins and minerals that are known to be necessary for normal physiological function. Practitioners also understand that appropriate additional amounts of vitamin and mineral ingredients need to be provided to nutritional compositions to compensate for some loss during processing and storage of such compositions. Additionally, the practitioner understands that certain micronutrients may have potential benefit for people with diabetes such as chromium, carnitine, taurine and vitamin E and that higher dietary requirements may exist for certain micro nutrients such as ascorbic acid due to higher turnover in people with diabetes.

An example of the vitamin and mineral system for a nutritional formulation used as a meal replacement typically comprises at least 20% of the RDI for the vitamins A, $B_1$, $B_2$, $B_6$, $B_{12}$, C, D, E, K, beta-carotene, biotin, folic acid, pantothenic acid, niacin, and choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients m-inositol, carnitine and taurine in a single serving or from about 50 Kcal to about 1000 Kcal.

Artificial sweeteners may also be added to the nutritional formula to enhance the organoleptic quality of the formula. Examples of suitable artificial sweeteners include saccharine, aspartame, acesulfame K and sucralose. The nutritional products of the present invention will also desirably include a flavoring and/or color to provide the nutritional products with an appealing appearance and an acceptable taste for oral consumption. Examples of useful flavorings typically include, for example, strawberry, peach, butter pecan, chocolate, banana, raspberry, orange, blueberry and vanilla.

The nutritional products of this invention can be manufactured using techniques well known to those skilled in the art. While manufacturing variations are certainly well known to those skilled in the nutritional formulation arts, a few of the manufacturing techniques are described in detail in the Examples. The manufacturing process is such to minimize the exposure of the soluble fiber to heat and shear to preserve the functionality. Generally speaking an oil blend is prepared containing all oils, any emulsifier, stabilizer and the fat soluble vitamins. Three more slurries (protein and two carbohydrate) are prepared separately by mixing a part of the carbohydrate and minerals together, the remaining carbohydrate with the fiber and the protein in water. The protein in water and carbohydrate/mineral slurries are then mixed together with the oil blend. The resulting mixture is homogenized, heat processed, standardized with water soluble vitamins, flavor and the carbohydrate/fiber blend. The final blend is homogenized and aseptically filled in to appropriate containers. Alternatively, the homogenized formula may be kept undiluted and dried to form powder. The product is then packaged. Typically the package will provide directions for use by the end consumer (i.e. to be consumed by a diabetic, to assist with weight loss, etc.).

A third embodiment of the instant invention is a method of blunting the postprandial glycemic response in a human by feeding the induced viscosity fiber system described above. The inventors discovered, in Experiment 5, that the polymer controlled induced viscosity fiber system provided a means to maintain blood glucose levels by reducing the early phase excursion and by appropriately maintaining the later phase excursion in healthy nondiabetic humans.

A fourth embodiment of the instant invention is a method of promoting the feeling of fullness in a human by feeding the induced viscosity fiber system described above. The inventors discovered, in Experiment 6, that nutritional products containing two levels of the polymer controlled induced viscosity fiber system (0.78% galactomannan and 1.21% galactomannan) delayed gastric emptying when compared to the control.

The embodiments of the present invention may, of course, be carried out in other ways than those set forth herein without departing from the spirit and scope of the invention. The present embodiments are, therefore, to be considered in all respects as illustrative and not restrictive and that all changes and equivalents also come within the description of the present invention. The following non-limiting Examples will further illustrate the present invention.

Experiment 1

Initial experimentation involved the viscosity measurements of various levels of hydrolyzed maltodextrin in a 2% guar gum solution.

A 2% guar gum solution was prepared by dispersing the dry gum powder in water using a Waring blender at high speed for 30 seconds. The resulting mixture was allowed to rest for at least 4 hours to allow the entrained air to escape. Graded amounts of various maltodextrins were added to the vortex of a 2% guar gum solution in a Waring blender. The viscosities of the mixtures were measured using a Brookfield Viscometer (Model DV-II+) with a 62 spindle at room temperature immediately after the maltodextrins were dispersed.

The solubility of guar gum was depressed to varying degrees by the addition of maltodextrins as indicated by the decrease in viscosity in FIG. 1. The effectiveness of maltodextrins in reducing the viscosity of the guar gum solution was inversely correlated with the molecular weight of the maltodextrin. As seen in FIG. 1, 10% of the larger molecular weight, DP 100, maltodextrin was sufficient to render guar gum insoluble while it took 15% of the smaller molecular weight, DP 25, maltodextrin to push the initially dissolved guar gum out of solution.

Experiment 2

Figure 2:
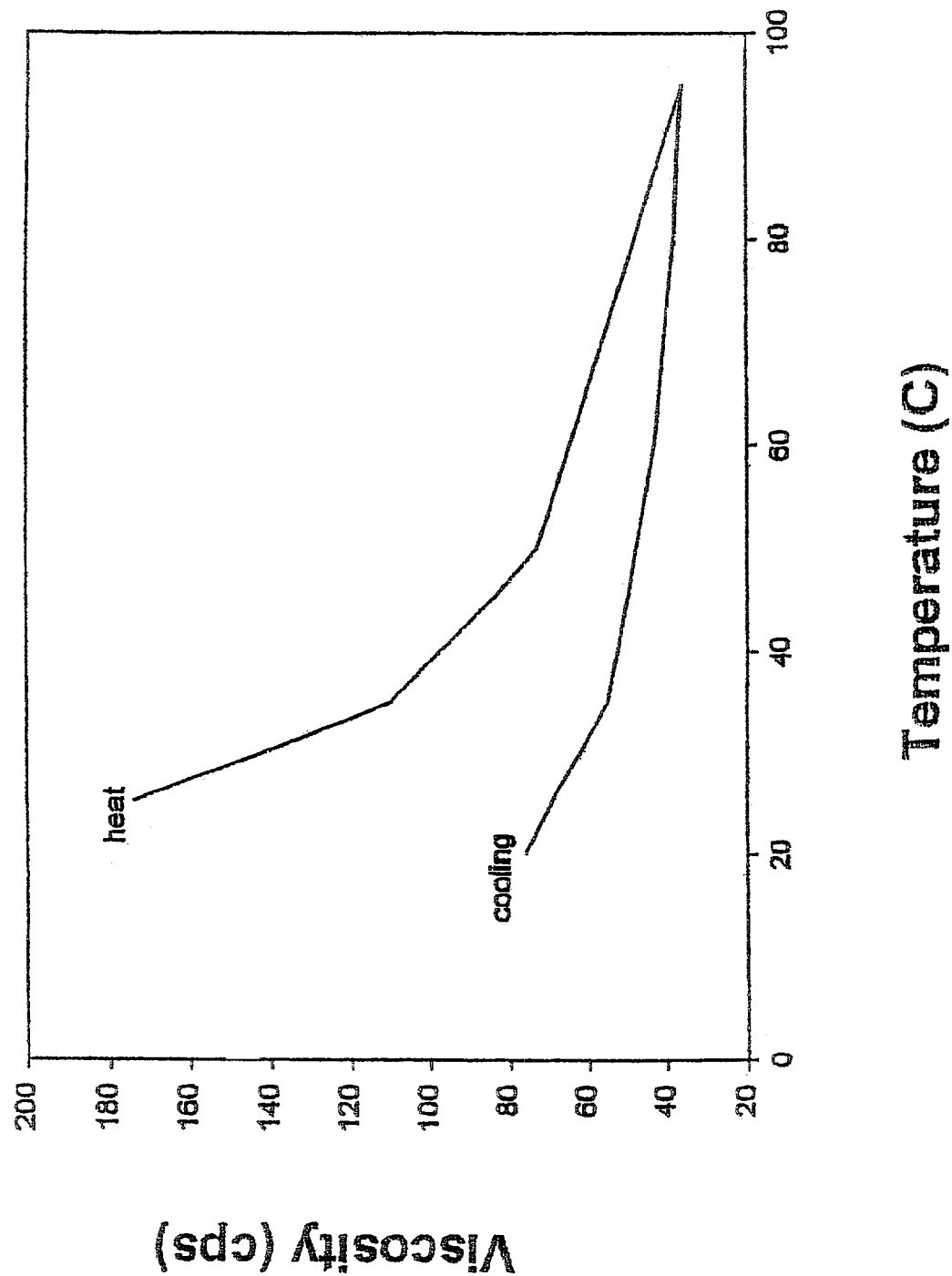
FIG. 2: Effect of heating and cooling on the viscosity of a 2% guar gum plus 10% DE 1 maltodextrin mixture.

The 10% DP 100 maltodextrin (Steer DR1 is a commercial DE1 maltodextrin from AE Staley Company) and 2% guar gum solution from Experiment 1 was heated to 95° C. and then allowed to cool to room temperature. The viscosity was monitored during the heating and cooling cycle using a Brookfield Viscometer (Model DV-II+) with a 62 spindle at room temperature (FIG. 2). The viscosity of the maltodextrin/guar gum dispersion was reduced from over 170 cpc to about 80 cps after heating and cooling to room temperature. Heat helped to drive the guar gum out of solution thereby decreasing the viscosity.

Twenty micro liters of bacterial alpha amylase (Sigma) was added to 250 gm of the maltodextrin/guar gum dispersion followed by shearing using a Glass-Col mixer for 30 minutes. The viscosity following shearing was measured using a Brookfield Viscometer (Model DV-II+) with a 62 spindle at room temperature. The viscosity of the maltodextrin/guar gum dispersion increased to over 14,000 cps after the mixture was treated with alpha-amylase.

Experiment 3

Maltodextrin (15% DP100) was added to various neutral gum solutions and the viscosities of the resultant mixtures were measured. Locust bean gum, Konjac flour, and methocel 2% solutions were prepared by dispersing the dry gum powder in water using a Waring blender at high speed for 30 seconds. The resulting mixtures were allowed to rest for at least 4 hours to allow the entrained air to escape. The viscosity of the mixtures were measured using a Brookfield Viscometer (Model DV-II+) with a 62 spindle at room temperature. The maltodextrin (15% DP100) was added to the vortex of each solution in a Waring blender. The viscosities of the mixtures were measured using a Brookfield Viscometer (Model DV-II+) with a 62 spindle at room temperature immediately after the maltodextrin was dispersed.

The addition of maltodextrin drastically reduced the viscosities of locust bean gum, konjac flour and methocel solutions. The viscosity of the locust bean gum solution dropped form 4000 cps to 1340 cps. The viscosity of the methocel solution dropped from 1370 cps to 28 cps. The 2% knojac flour solution gelled, however the addition of maltodextin dropped the viscosity to 363 cps.

Additionally, the viscosity of locust bean gum/maltodextrin solution was about 1000 cps, which decreased to less than 100 cps after the dispersion was allowed to rest overnight. These findings indicated that the time for the dissolved polymer to come out of solution may vary but all neutral water soluble polymers are suitable candidates for developing polymer controlled induced viscosity products.

Experiment 4

Various proteins (4.4% by weight) were added to a model system containing 0.13% K-citrate, 0.15% Na-citrate, 0083% $K_2HPO_4$, 9.4% DP 100 maltodextrin and 1% guar gum at room temperature under vigorous agitation. The viscosity of the mixtures were measured using a Brookfield Viscometer (Model DV-II+) with a 62 spindle at room temperature. The mixtures were autoclaved (120° C. for 30 minutes), allowed to cool, then digested with alpha-amylase. Twenty micro liters of bacterial alpha amylase (Sigma) was added to 250 gm of the autoclaved mixtures followed by shearing using a Glass-Col mixer for 30 minutes. The viscosity following shearing was measured using a Brookfield Viscometer (Model DV-II+) with a 62 spindle at room temperature (Table 1).

TABLE 1

Effect of protein source on the development of viscosity

| Protein Source | W/O Enzyme (cps) | After Enzyme (cps) |
|---|---|---|
| No protein | 29.0 | 14,000 |
| Insoluble casein | 72.5 | >>15,000 |
| Insoluble milk protein isolate | 95.5 | >>15,000 |
| Soluble casein | 104 | >15,000 |
| Insoluble soy protein | 125 | >15,000 |
| Soluble sodium caseinate | 166 | 380 |
| Soluble whey | 150 | 350 |

All of the soluble proteins, with the exception of soluble casein (Alanate 166 from New Zealand Milk Products in Santa Rosa, Calif.), reduced the induced viscosity of the unsterile model systems. The soluble proteins form large aggregates after autoclaving. A Warring blender was used to break down the aggregates. Surprisingly, the sterilized model systems containing sodium caseinate or whey protein produced a low induced viscosity (less than 400 cps) after alpha-amylase digestion. The viscosities of the alpha-amylase digested model systems containing sodium caseinate increased to 2,800 cps after it was subsequently digested with Pronase (a mixture of proteases from Sigma). Apparently, some of the guar gum was trapped in the protein aggregates during autoclaving. The trapped guar gum was released after the protein aggregates were broken down by the Pronase. However, the fact that the induced viscosity of the Pronase digested model system was lower than that of the unsterile model (2,800 vs 4,700 cps) lead the inventors to suspect that a portion of the guar gum molecules were hydrolyzed during the autoclaving. To test this, the model system without protein was autoclaved twice. The resulting induced viscosity was reduced from 14,000 cps to 4,100 cps after going through the additional autoclave cycle, confirming that some of the guar gum was degraded during retorting. Thus, a short exposure to heat is preferred to maximize the induced viscosity.

Addition of an insoluble protein such as milk protein isolate to the guar/maltodextrin model system increased the induced viscosity. The insoluble protein particles absorb a lot of water and increase the effective volume fraction of solids, thus producing a positive impact on the viscosity of the dispersion. The preferred protein system is a blend of soluble and insoluble protein.

It is well known in the art that mechanical shear can cause hydrocolloid molecules to degrade. The autoclaved model system was sheared using a tissue grinder for one minute and found that the shearing reduced the induced viscosity over 30,000 cps to less than 4,000 cps. Therefore, the manufacturing process is such to minimize the exposure of guar gum to heat and shear to preserve the guar gum functionality.

Example I

The process for manufacturing 453.6 kg of a liquid nutritional containing the polymer controlled induced viscosity fiber system of the invention is described below. Most of the DE 1 maltodextrin was withheld from the carbohydrate/mineral slurry. The guar gum was added at standardization as a guar gum/maltodextrin dispersion to minimize exposure to heat and shear. Because the maltodextrin prevents the guar gum from dissolving, it was possible to produce a maltodextrin/guar gum dispersion with a manageable viscosity. Further, the addition of the DE 1 maltodextrin at standardization prevented the mix from forming a gel in the finished product tank (DE 1 maltodextrin can retrograde and form a gel at 4° C. if the concentration exceeds 3%).

The required amount of ingredients (Table 2) for the fat blend were combined and held.

TABLE 2

| Fat Blend | |
|---|---|
| High Oleic Safflower Oil | 8.2 kg |
| Canola Oil | 0.95 kg |
| Soy Lecithin | 0.49 kg |
| Vitamin DEK premix* | 30.87 gm |
| Beta Carotene 30% | 3.63 gm |
| Vitamin A Palmitate | 3.41 gm |
| Gum Arabic | 1.7 kg |

*per gm Vitamin DEK premix: 8130 IU vitamin $D_3$, 838 IU vitamin E, 1.42 mg vitamin $K_1$ The required amount of ingredients (Table 3) for the protein in water slurry were combined. The pH was adjusted to 6.6–6.8 using 1 N KOH. The pH adjusted blend was held.

TABLE 3

| Protein in Water Slurry | |
|---|---|
| Water | 177 kg |
| Milk Protein Isolate | 12.8 kg |
| Sodium Caseinate | 32 kg |

The required amount of ingredients (Table 4) for the carbohydrate/mineral slurry were combined and the pH was adjusted to 6.6–6.8 using 1 N KOH. The pH adjusted blend was held.

TABLE 4

| Carbohydrate/Mineral Slurry | |
|---|---|
| Water | 29 kg |
| Maltodextrin DE 1 | 11 kg |
| Fructose | 2.7 kg |
| Micronized TCP | 1.3 kg |
| Magnesium Chloride | 1.1 kg |
| Sodium Citrate | 1.1 kg |
| Potassium Phosphate Dibasic | 0.99 kg |
| Magnesium Phosphate Dibasic | 0.54 kg |
| Potassium Citrate | 363.2 gm |
| UTM/TM Premix* | 172.5 gm |
| Potassium Iodide | 0.11 gm |

*per gm of UTM/TM premix: 83 mg zinc, 65 mg iron, 18 mg manganese, 7.8 mg copper, 0.262 mg selenium, 0.365 mg chromium, 0.585 molybdenum.

After each slurry was prepared, the carbohydrate/mineral slurry was added to the protein in water slurry. The blend pH was adjusted to 6.6–6.8. The fat blend was then added. The final blend was processed at UHT temperatures (295° F. for 5 seconds) and homogenized at 4000 psi.

The required amount of ingredients (Table 5) for the vitamin solution were combined and the pH was adjusted to 6.5–7.5 using 45% KOH. The pH adjusted blend was held.

TABLE 5

Vitamin Solution

| | |
|---|---|
| Water | 8.5 kg |
| Ascorbic Acid | 227 gm |
| Choline Chloride | 181.6 gm |
| L-Carnitine | 49.9 gm |
| WSV Premix* | 40.9 gm |
| Taurine | 45.4 gm |
| Sucralose | 74.9 gm |
| Vanilla Flavor | 2.0 kg |

*per gm of WSV premix: 375 mg niacinamide, 242 mg calcium pantothenate, 8.4 mg folic acid, 62 mg thiamine chloride, 48 mg riboflavin, 59 mg pyridoxine hydrochloride, 165 mcg cyanocobalamin, and 7305 mcg biotin The vitamin solution was added to the processed blend at standardization. The required amount of ingredients (Table 6) for the 1.3% guar gum solution were combined and held.

TABLE 6

Guar Gum Solution

| | |
|---|---|
| Water | 113 kg |
| Maltodextrin DE 1 | 25 kg |
| Guar Gum | 6 kg |

The guar gum solution was added to the standardized blend. Guar gum was added to the maltodextrin solution under high agitation to prevent build up of excessively high viscosity and guar gum lumps. Failure to disperse guar gum properly caused flow problems in the aseptic filling unit. The final blend was UHT heated to 295° F. for 5 seconds and homogenized at 1000 psi and aseptically filled into sterile 32 oz bottles.

The product manufactured as described above had an initial viscosity of 120 cps and developed an induced viscosity of over 14,000 cps upon treatment with alpha amylase.

Experiment 5

The primary objective of this study was to evaluate the efficacy of a polymer controlled induced viscosity fiber system (IV) on the attenuation of the postprandial glycemic excursion to a low DE maltodextrin beverage plus white bread (rapidly digested starches) in healthy nondiabetic individuals. A secondary objective was to evaluate the subjective gastrointestinal tolerance of subjects consuming a polymer controlled induced viscosity fiber system containing test meal. As an exploratory objective, the effects of a polymer controlled induced viscosity fiber system on satiety was evaluated.

This study was a randomized, double-blind, two group, placebo-controlled, crossover, single center study. Subjects participated in four 3-h meal glucose tolerance tests (MGTT) on separate occasions. Subjects were randomly assigned to treatment sequences. After an overnight fast, subjects consumed 50 g available carbohydrate (25 g from DE 1 maltodextrin and 25 g from white bread) as the MGTT. Two DE 1 maltodextrin beverages were formulated to test the effects of the polymer controlled induced viscosity fiber system.

To ensure that subjects had similar glycogen stores on the 4 test days, subjects were instructed to consume a high carbohydrate diet (minimum 150 g carbohydrate per day) for 3 d before each meal glucose tolerance test and were also asked to avoid exercise 24 h before the experiment. On the evening before each meal glucose tolerance test, all subjects consumed a low-residue dinner consisting of one 8 fl oz (237 ml) can of chocolate Ensure Plus® (Ross Products, Columbus, Ohio) with additional Honey Graham Crunch Ensure®) Bars (Ross Products, Columbus, Ohio) to provide one-third of each subject's individual daily caloric requirement as estimated by the Harris-Benedict equation multiplied by an activity factor of 1.3. Subjects were instructed to fast overnight, following their low-residue evening meal, during which they were only allowed to consume water. Smoking was prohibited. On the morning of each meal glucose tolerance test, body weight, body temperature, pulse rate and blood pressure were measured by standard procedures. A fasting finger-prick capillary blood sample was obtained and collected into fluoro-oxalate tubes after 30 min of rest. Subjects then consumed the appropriate test meal within 10 min. Finger-prick capillary blood was obtained at 0, 15, 30, 45, 60, 90, 120 and 180 minutes postprandial. Samples were stored at −20° C. for a maximum of 3 d until analysis of whole blood glucose. Whole blood glucose was analyzed by the glucose oxidase method utilizing a YSI analyzer (model YSI 2300 STAT PLUS, Yellow Springs Instruments, Yellow Springs, Ohio). Subjects were allowed 8 fl oz water (240 ml) during each 2-h test. Immediately following each trial body temperature, pulse rate and blood pressure were measured. Subjects returned on average within 9 d (range 5 to 42 d) for repeat analysis with the appropriate crossover treatment.

Using a questionnaire, subjects were asked to report the frequency and intensity of the following symptoms: nausea, cramping, distention, and flatulence for the 24-h period immediately following consumption of the test material. Intensity and frequency was set to a 100-mm linear visual analogue scale (0 representing "Absent" and 100 "Severe" and 0 representing "Usual" and 100 "More than usual," respectively). Subjects placed a single perpendicular slash mark across the 100 mm horizontal line to indicate their scores for each of these variables of frequency and intensity. A score of 5 or less was considered not physiologically meaningful.

In order to assess the subjective feeling of hunger, subjects completed a satiety questionnaire immediately before the MGTT, at 1, 2, and 3 h postprandial, and immediately before and after their lunch meal after the MGTT. Subjects rated their feeling of hunger with the following scale: 1=not at all hungry; 3=slightly hungry; 5=moderately hungry; 7=very hungry; 9=extremely hungry. In addition, subjects reported the amount of lunch consumed as: much less than usual, moderately less than usual, somewhat less than usual, slightly less than usual, about the same, slightly more than usual, somewhat more than usual, moderately more than usual, or much more than usual.

Subjects were between 18 and 75 years of age, inclusively, were male or a non-pregnant female at least 6 weeks postpartum and nonlactating, were not currently receiving oral contraceptives, had a body mass index (BMI) between 20 and 28 kg/m$^2$, did not have diabetes mellitus or glucose intolerance (baseline serum glucose <110 mg/dl (6.11 mmol/L)), did not have a family history (first degree relatives) of diabetes mellitus or glucose intolerance, were free from active metabolic or gastrointestinal diseases that may interfere with nutrient absorption, distribution, metabolism, or excretion and had no known food allergies, had no recent (<3 months) infections, surgeries or corticosteroid treatment and were not under a high level of stress, were willing to consume Ensure® Plus and Ensure® Bar(s) as the evening meal on the day prior to test; were willing to fast (10 hours)

prior to testing and were willing to consume the product within a 10-minute period; abstained from exercise 24 hours prior to testing and minimized activity during the test; were not taking daily medications (e.g., acetaminophen, salicylates, diuretics, etc.) that would interfere with nutrient absorption, metabolism, excretion or gastric motility; and had voluntarily signed an informed consent form prior to any participation in the study.

Subjects consumed 50 g available carbohydrate: 25 g from DE 1 maltodextrin (Star D, A. E. Staley Manufacturing Co., Decatur, Ill.) and 25 g from white bread as the MGTT. Two DE 1 maltodextrin-based beverages were formulated to test the effects of the polymer controlled induced viscosity fiber system (Table 7).

TABLE 7

Composition of Products

|  | Control | IV |
|---|---|---|
| Ingredient composition | g/100 g product | |
| Water | 89.39 | 87.31 |
| DE 1 maltodextrin | 10.42 | 10.42 |
| Guar gum | 0 | 2.08 |
| Fructose | 0 | 0 |
| Orange flavor | 0.12 | 0.12 |
| Sucralose | 0.07 | 0.07 |
| Proximate analysis | g/100 g product | |
| Total solids | 9.5 | 11.8 |
| Carbohydrate | 9.5 | 11.7 |
| Fructose | 0 | 0 |
| TDF | 0 | 1.80 |
| Galactomannan | 0 | 1.53 |
| Nutrient | g/240 g serving | |
| Fructose | 0 | 0 |
| TDF | 0 | 4.32 |
| Galactomannan | 0 | 3.67 |
| Maltodextrin by difference | 22.80 | 23.76 |
| Viscosity, cps | 8 | 156 |

White bread was made from the following recipe: 250 ml warm water, 334 g all purpose flour (e.g., Robin Hood), 7 g sugar (sucrose), 4 g salt, 6.5 g dry instant yeast. The bread maker was set for a 2 h bake, and turned on. After the bread was made, it was removed from the container, set for 1 h, and weighed. Each loaf contained 250 g carbohydrate, giving ten 25-g carbohydrate portions. The end crusts were discarded, so eight portions were available for the meal glucose tolerance test.

The primary variable was the peak incremental change from baseline in blood glucose concentration.

The secondary variables were positive incremental area under the glucose curve, time to peak blood glucose concentration, and the incremental change from baseline in blood glucose concentration at individual time points.

The supportive variables were: demographic variables [age, sex, race, and expected energy expenditure (kcal/d)]; anthropometric variables [height, weight, and BMI (computed centrally)]; intensity and frequency of gastrointestinal intolerance symptoms (nausea, cramping, distention, and flatulence); glycemic index; percentage of subjects with a positive breath hydrogen test; breath hydrogen and methane concentration at individual time points; daily medications; and satiety factors.

Subjects had a mean (±SE) age of 51±3 years (range: 18 to 75 years), weight of 68.4±1.8 kg (range: 55.4 to 84.0 kg), and body mass index of 24.2±0.4 kg/m$^2$ (range: 20.2 to 27.9 kg/m$^2$). Subjects did not have active gastrointestinal or metabolic diseases, a first-degree family history of diabetes mellitus or glucose intolerance, recent infection, surgery or corticosteroid treatment. No subjects were receiving oral contraceptives.

Results

Table 8 presents data for incremental (i.e., change from baseline) peak glucose concentration, positive incremental area under the glucose curve, time to peak glucose concentration, and glycemic index.

TABLE 8

Subjects consuming novel carbohydrate beverages in a meal glucose tolerance test

|  | Treatment | |
|---|---|---|
|  | Control | IV |
| Incremental peak glucose mmol/L[‡] | 4.2 ± 0.28[a] | 2.2 ± 0.16[b] |
| Time to peak (min)[‡] | 42 ± 2.3[b] | 68 ± 5.0[a] |
| Incremental AUC mmol · min/L)[‡] | 283 ± 22[a] | 215 ± 19[b] |
| Glycemic index[§] | 100 | 80 ± 5.8 |

*Mean ± SEM.
[‡]Treatment effect, P < 0.01.
[§]Glycemic index = incremental AUC for treatment/incremental AUC for control
[a,b]Means in the same row with unlike superscript letters differ (P < 0.05).

The mean fasting blood glucose concentration was not different between treatments. Peak incremental blood glucose concentration was lower (P<0.05) when subjects consumed the test meal containing polymer controlled induced viscosity fiber system compared with the Control. Incremental area under the glucose curve was lower (P<0.05) when subjects consumed the polymer controlled induced viscosity fiber system containing products compared with when subjects consumed Control. Time to peak glucose concentration was delayed (P<0.05) when subjects consumed IV compared with the Control. The glycemic index was 80±5.8 for polymer controlled induced viscosity fiber system. When subjects consumed test meals containing polymer controlled induced viscosity fiber system, the postprandial rise in blood glucose was reduced (P<0.05) at 15, 30, 45, and 60 min. In addition, there was a slower late postprandial decrease in blood glucose as shown by higher (P<0.05) blood glucose concentrations at 120 and 180 min, indicating slower and prolonged carbohydrate absorption.

Subjective reports of gastrointestinal symptoms (intensity and frequency of nausea, cramping, distention and flatulence) 24 h post MGTT are presented in Table 9.

TABLE 9

Gastrointestinal tolerance of subjects consuming carbohydrate beverages in a meal glucose tolerance test

|  | Treatment | |
|---|---|---|
|  | Control | IV |
| Intensity of |  |  |
| Nausea | 1 ± 0.2 | 1 ± 0.3 |
| Cramping | 1 ± 0.5 | 5 ± 2.9 |
| Distension | 0 ± 0.2 | 4 ± 2.6 |
| Flatulence | 2 ± 1.7 | 5 ± 3.0 |

TABLE 9-continued

Gastrointestinal tolerance of subjects consuming carbohydrate beverages in a meal glucose tolerance test

| | Treatment | |
| --- | --- | --- |
| | Control | IV |
| Frequency of | | |
| Nausea | 0 ± 0.2 | 1 ± 0.4 |
| Cramping | 0 ± 0.2 | 5 ± 3.0 |
| Distension | 1 ± 0.2 | 2 ± 1.5 |
| Flatulence | 2 ± 1.7 | 6 ± 3.2 |

*Mean ± SEM, A score of 5 or less was considered not physiologically meaningful.

Subjects reported a higher intensity and frequency of cramping, distension, and flatulence when they consumed the polymer controlled induced viscosity fiber system containing products. The relatively large standard errors indicate that certain individuals were more susceptible than others.

Subjective ratings of hunger during the 3-h MGTT and immediately before and after their lunch meal were similar among groups. In addition, the estimated amount of food consumed during the lunch meal following the MGTT was similar among groups.

Conclusion

In conclusion, polymer controlled induced viscosity fiber system provided a means to maintain blood glucose levels by reducing the early phase excursion and by appropriately maintaining the later phase excursion in healthy nondiabetic humans. Healthy nondiabetic subjects reported a higher intensity and frequency of cramping, distension, and flatulence when they consumed the polymer controlled induced viscosity fiber system containing products.

Experiment 6

The objectives of this animal study were to determine the effect of a nutritional product containing the polymer controlled induced viscosity fiber system (IV) of the instant invention on gastric emptying, gastrointestinal motility, and glycemic response. Specifically, these objectives were met by determining the effect of the IV containing product on myoelectrical activity of the stomach, small intestine and colon. Parameters that were analyzed included: the percentage of regular slow waves, the percentage of dysrhythmia, the frequency and amplitude of the slow wave, the coupling and propagation of the slow wave. The effect of the IV containing product on contractility of the stomach, pylorus, small intestine and colon was also determined. Additionally, the effect of an IV containing product on gastric emptying was evaluated.

Eight healthy adult female, mongrel dogs weighing between 19 and 27 kg were used in this study. After an overnight fast, each dog was operated under anesthesia. Four pairs of Teflon coated 28 gauge stainless steel cardiac pacing electrodes (A&E Medical, Farmingdale, N.J.) were implanted on the serosal surface of the stomach along the greater curvature at intervals of 4 cm. The most distal pair was located 2 cm above the pylorus. Electrode pair number 1 (channel 1) was located in the body of the stomach; electrode pair number 4 (channel 4) was located in the distal antrum of the stomach. The distance between the two electrodes in a pair was 0.5 cm. The electrodes were brought out percutaneously through the abdominal wall. An intestinal fistula was made in the duodenum (20 cm beyond the pylorus). This fistula was used to collect gastric contents for the determination of gastric emptying. In addition to the gastric electrodes, two pairs of serosal electrodes were implanted in the jejunum (at 35 cm and 40 cm from the pylorus). These electrodes were used to assess myoelectrical activity of the jejunum. After surgery, dogs were transferred to a recovery cage. All studies were initiated when each dog had completely recovered from the surgery.

Products were formulated to contain the following caloric distribution: 29% kcal from fat, 20% kcal from protein, and 51% kcal from carbohydrate. Products were manufactured into 1-L ready-to-feed bottles under aseptic conditions. Product caloric density (0.677 kcal/ml) was such that 325 ml (11 fl oz) delivered 28 g of available carbohydrate. Three experimental products were tested: control with no galactomannan; formula with 0.78% galactomannan (about 2.5 g); formula with 1.21% galactomannan (about 3.9 g).

This study was a controlled, randomized, three-way crossover. Each dog received each treatment, with a minimum of three days between each test. The order of consumption of the products was randomized. Myoelectrical activity was recorded to establish baseline activity. After this baseline recording, the animal was fed the appropriate study product (325 ml of product, which supplied 220 kcal). Following the feeding, myoelectrical activity was recorded and gastric emptying was measured for 120 minutes. In addition, a 5 ml subsample of each gastric emptying collection was obtained and transferred into a 15 ml centrifuge tube. Samples were quick frozen and stored at approximately −70 C. These samples were shipped to Ross Products Division for analysis of rheological characteristics.

Gastric Emptying

Each test meal was mixed with 137.1 mg phenol red. The emptied chyme was collected from the duodenal cannula at 15-minute intervals for the duration of the study. The rate of gastric emptying was assessed by determining the volume of chyme and the concentration of the phenol red in each collection.

Gastric and Small Bowel Motility

Gastric motility and small bowel motility was assessed by calculating spike activity detected from the myoelectrical recording. In this experiment, two parameters were used: 1) number of bursts per minute (NBPM): this is an indication of the number of contractions per minute; and 2) number of spikes per minute (NSPM): a sum of total number of spikes per minute, reflecting the strength of contractions.

Gastric Slow Waves

Gastric Slow Waves were recorded from the four pairs of implanted serosal electrodes using a multi-channel recorder (Acknowledge III, EOG 100A, Biopac Systems, Inc. Santa Barbara, Calif.) with a cutoff frequency of 35 Hz. All signals were digitized at a frequency of 100 Hz and stored electronically. Recorded signals were filtered using a digital low pass filter with a cutoff frequency of 1 Hz and down sampled at 2 Hz. Spectral analysis was performed on the recordings and the following parameters were determined:

1. Dominant Frequency and Power: The frequency at which the power spectrum of an entire recording had a peak power in the range of 0.5 to 9.0 cycles per minute is defined as the dominant frequency. The power corresponding to the dominant frequency in the power spectrum is defined as the dominant power. Decibel (dB) units were used to represent the power of the gastric slow wave. The relationship of the power P in dB and power P' in the linear scale is as follows: $P=10*\log_{10}(P')$. A negative value in the power reflects a power between 0 and 1 in the linear scale.

2. Percentage of Normal Slow Waves: This parameter specifies the regularity of gastric slow waves. In this method, the gastric myoelectrical recording is divided into 1-minute segments. The 1-minute segment of the recording is defined as normal if its power spectrum had a clear peak in the 4–6 cycles per minute frequency range. Otherwise it was defined as abnormal. The percentage of normal gastric slow waves was determined by computing the ratio between the number of normal segments and the total number of segments. The normal frequency range was defined as 4–6 cycles per minute. The value of the percentage of normal slow waves presented in the result section is an average among the 4 channels.

3. Percentage of Slow Wave Coupling: A cross-spectral analysis method was used to calculate the percentage of slow wave coupling among the 4-channel recordings. It was computed on a minute-by-minute basis. First, the adaptive running spectral analysis was performed on each channel minute-by-minute, and the dominant frequency of the slow wave in each minute of the recording was derived. The corresponding dominant frequencies of the slow wave between any two channels were then compared minute-by-minute. The minute of the slow wave recorded on the two channels was defined as coupled if their dominant frequencies were both within the normal frequency range and their difference was less than 0.2 cycles per minute. The percentage of slow wave coupling is defined as the ratio between the number of the time segments during which the recorded slow waves were coupled and the total number of segments. The value presented in the result section is an average over the exhaustive comparisons among the 4 channels.

Intestinal Slow Waves

Intestinal Slow Waves were recorded using the implanted serosal electrodes and analyzed as described above, and the following parameters were determined: 1) Dominant Frequency and Power; and 2) Percentage of Normal Slow Waves.

Rheological Properties of Chyme

A 5 ml subsample of each 15-minute duodenal collection was obtained and transferred into a 15 ml centrifuge tube. Samples were quick frozen in ethanol and dry ice and stored at –70° C. Samples were shipped to Ross Products Division for analysis of rheological characteristics.

Viscosity was measured at 37 C with a controlled stress rheometer (Model CSL2-50, TA Instruments, New Castle, Del.) using a 4 cm 4 degree cone. Shear rate was swept from 1 to 250 sec$^{-1}$ over 2 seconds. A 1 ml sample was used for each viscosity measurement. Because some of the samples contained particulate matter, they were centrifuged slightly at low rpm to force the larger particles to the bottom of the tube. The upper layers were mixed by hand before sampling.

In vitro viscosity was determined by adding 20 pl of alpha-amylase (Sigma # A 3306) to 250 grams of product. This was then incubated at 40° C. for 30 minutes. At the end of 30 minutes, the mixture was agitated at low rpm for 30 seconds. Viscosity was then measured as described above.

Results

Figure 3:
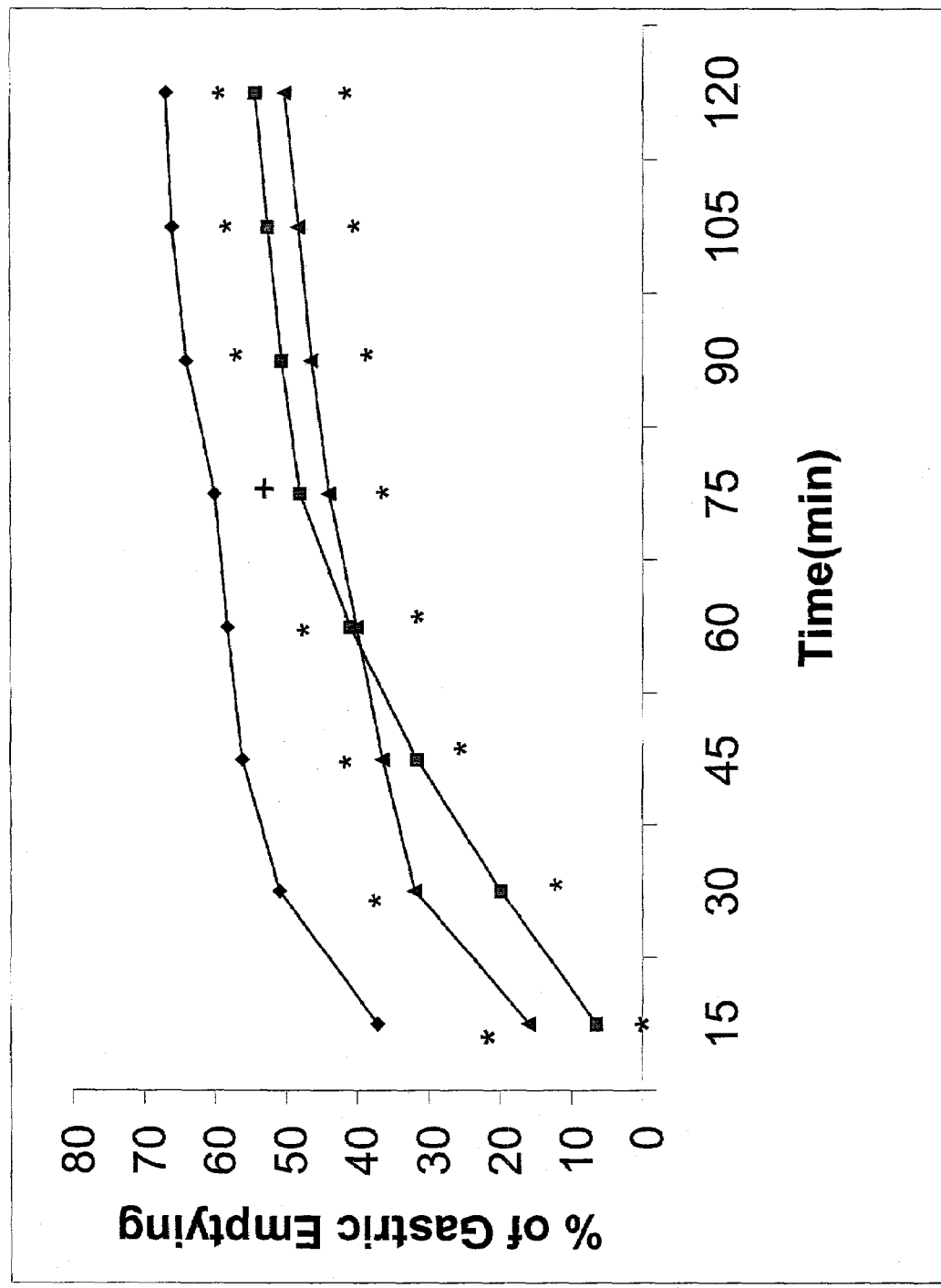
FIG. 3: Effect on gastric emptying of control formula(♦), 0.78% glactomannan formula(■) and 1.21% glactomannan formula(▲). *P<0.05 vs control; +P=0.095 vs control.

Gastric emptying was significantly delayed by both 0.78% galactomannan and 1.21% galactomannan containing products starting from minute 15 compared with the control session ($p<0.02$,ANOVA) (see FIG. 3).

The NBPM did not show any significant postprandial change in any of the treatments. Neither was there a difference at any postprandial period. among the 3 treatments. These data suggest that the frequency of gastric contractions was not affected by the ingestion of the test meal or the composition (fiber) of the meal.

The NSPM (strength of contractions) was significant increased postprandially (during the first hour) in the control session but not in the other treatment sessions. There was no significant difference in the NSPM at any time among the 3 treatments.

Figure 4:
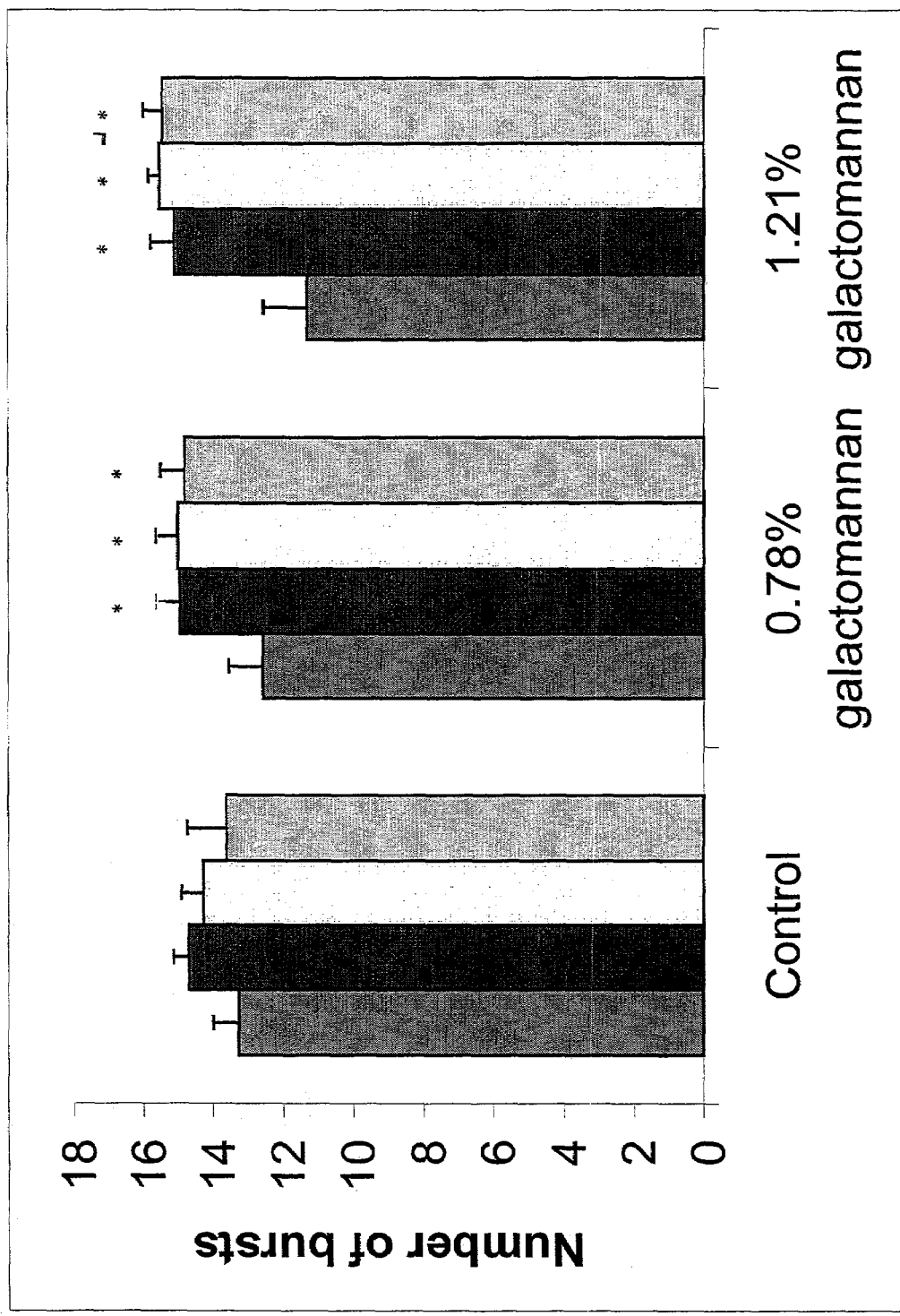
FIG. 4: Effects on the frequency of intestinal contractions of control formula, 0.78% glactomannan formula and 1.21% glactomannan formula at baseline(charcoal gray), 0–30 minutes(black), 31–60 minutes(white) and 91–120 minutes (gray). *P<0.05 vs baseline.

A significant postprandial increase ($p<0.05$) was noted in the NBPM (frequency of intestinal contractions) with 0.78% and 1.21% of galactomannan. This increase was however, absent in the control session (see FIG. 4). No difference was observed in the NBPM at any recording time among the 3 treatments.

Figure 5:
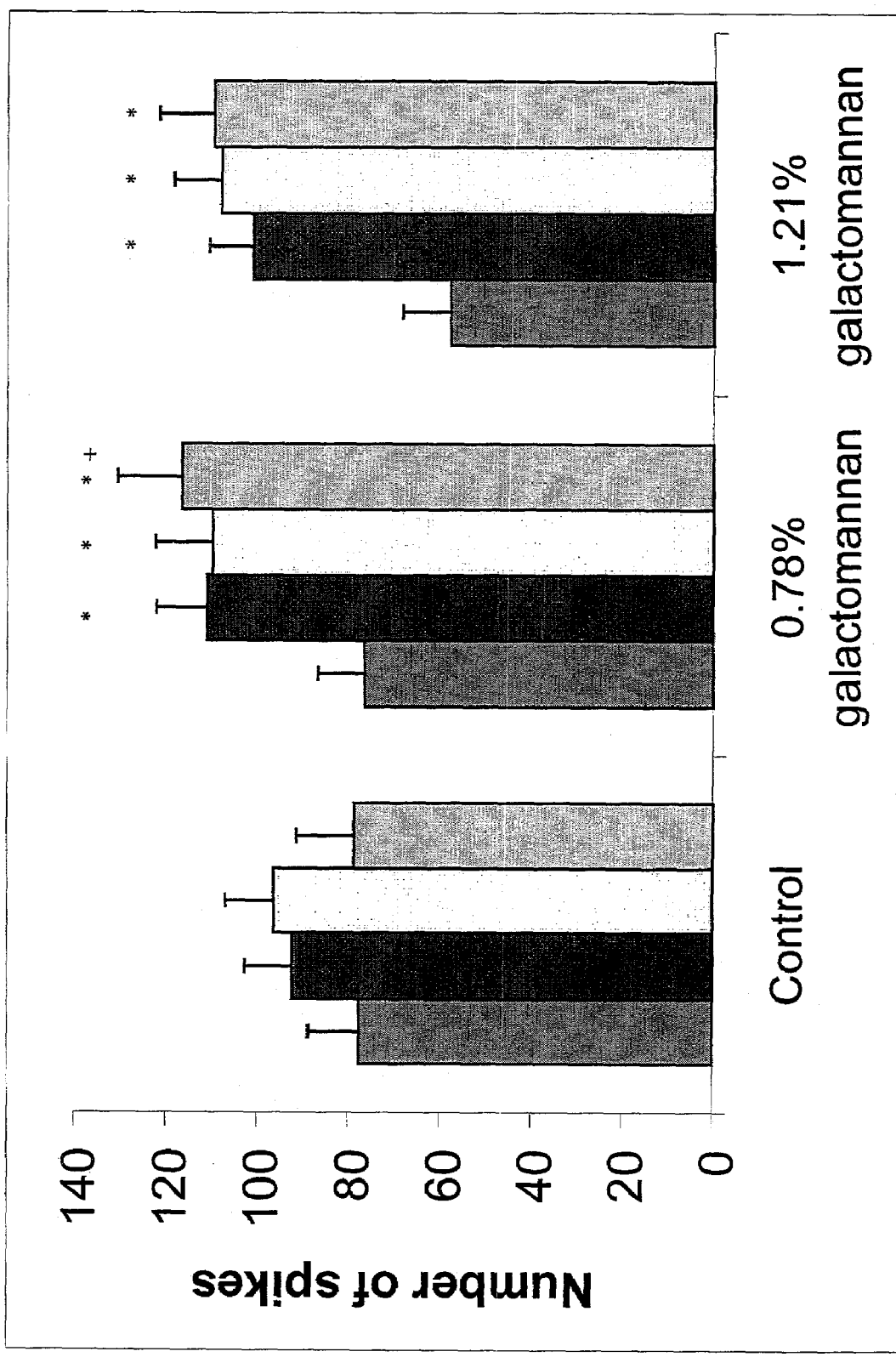
FIG. 5: Effects on the strength of intestinal contractions of control formula, 0.78% glactomannan formula and 1.21% glactomannan formula at baseline(charcoal gray), 0–30 minutes(black), 31–60 minutes(white) and 91–120 minutes (gray). *P<0.05 vs baseline; +P<0.05 vs control.

Similarly, there was a significant increase ($p<0.05$) in the NSPM (strength of intestinal contractions) with 0.78% and 1.21% of galactomannan but not in the control session. In addition, the NSPM during the last 30 minutes of the postprandial recording with 0.78% of galactomannan was significantly higher than that in the corresponding period of the control session (see FIG. 5).

The dominant frequency of gastric slow waves did not show any significant postprandial change in any of the treatments. Neither was there a difference at any postprandial period among the 3 treatments. These data suggest that the dominant frequency of gastric slow waves was not affected by the ingestion of the test meal or the composition (fiber) of the meal.

The dominant power of gastric slow waves did not show any significant postprandial change in any of the sessions. Neither was there a difference at any postprandial period among the 3 treatments. These data suggest that the amplitude of gastric slow waves was not affected by the ingestion of the test meal or the composition (fiber) of the meal.

The percentage of normal slow waves did not show any significant postprandial change in any of the sessions. Neither was there a difference at any postprandial period among the 3 treatments. These data suggest that the regularity of gastric slow waves was not affected by the ingestion of the test meal or the composition (fiber) of the meal.

Slow wave coupling did not show any significant postprandial change in any of the sessions. Only the slow wave coupling during the last 30 minutes of the postprandial recording with 1.21% of galactomannan was significantly higher than that in the corresponding period of the control session. These data imply that the test meal or the composition (fiber) of the meal did not affect the propagation of gastric slow waves during one hour after meal.

Intestinal slow waves were recorded using 2 pairs of small bowel electrodes and the data presented below reflect the averaged values between the 2 channels.

Small bowel dominant frequency did not show any significant postprandial change in any of the sessions. Neither was there a difference at any postprandial period among the 3 treatments. These data suggest that the dominant frequency of intestinal slow waves was not affected by the ingestion of the test meal or the composition (fiber) of the meal.

The dominant power of intestinal slow waves did not show any significant postprandial change in any of the sessions. Neither was there a difference at any postprandial period among the 3 treatments. These data suggest that the amplitude of intestinal slow waves was not affected by the ingestion of the test meal or the composition (fiber) of the meal.

Percentage of normal slow wave in the small bowel didn't change in any of the study sessions after meal compared with fasting state. Neither was there a difference at any postprandial period among the 3 treatments. These data suggest that the regularity of intestinal slow waves was not affected by the ingestion of the test meal or the composition (fiber) of the meal.

Figure 6:
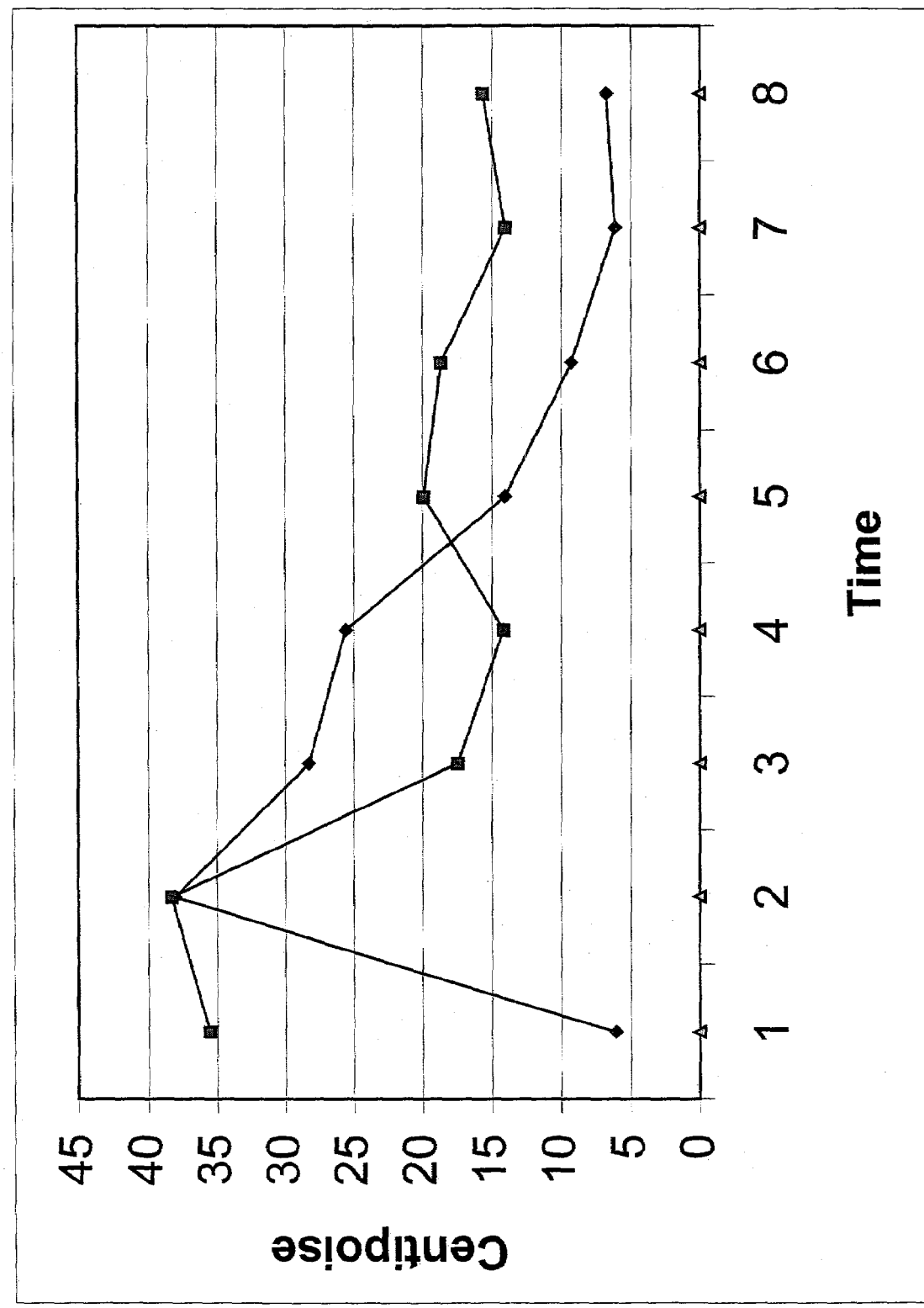
FIG. 6: Viscosity at a shear rate of 30 sec$^{-1}$ vs collection time of control formula(Δ), 0.78% glactomannan formula (♦) and 1.21% glactomannan formula(■).

FIG. 6 plots the mean viscosity of the studied formulas at a shear rate of 30 sec$^{-1}$ at each collection time. It can be seen that the mean viscosity of the 0.78% galactomannan and 1.2% galactomannan is greater than the control product.

The in vitro viscosity of the 0.78% galactomannan product at a shear rate of 30 sec$^{-1}$ was 706 cps, for the 1.2% galactomannan product this value was 890 cps.

Conclusions

The results showed that the induced viscosity products (both 0.78% galactomannan and 1.21% galactomannan) delayed gastric emptying. In addition, there was a postprandial enhancement of small bowel (but not gastric) motility with these products, which was not seen in the control session.

We claim:

1. A polymer controlled induced viscosity fiber system comprising guar gum and DP 100 maltodextrin in a ratio of from 1 to 5, wherein said fiber system generates an in vivo viscosity of greater than 300 cps when exposed to alpha amylase.

2. The polymer controlled induced viscosity fiber system of claim 1, wherein the induced viscosity system is a meal replacement beverage.

3. The polymer controlled induced viscosity fiber system of claim 2, wherein the meal replacement beverage comprises:
   (a) from about 10% to about 35% protein as a percentage of total calories,
   (b) from about 10% to about 37% fat by weight of total calories, and
   (c) from about 25% to about 75% carbohydrates as a percentage of total calories.

4. The polymer controlled induced viscosity fiber system of claim 3, wherein the polymer controlled induced viscosity fiber system represents from 10% to 60% by weight of the carbohydrate, on a dry weight basis.

5. The polymer controlled induced viscosity fiber system of claim 4, wherein the beverage comprises at least about 1 w/w % guar gum.

* * * * *